(12) United States Patent
Helmer (10) Patent No.: US 10,512,727 B2
(45) Date of Patent: Dec. 24, 2019

(54) ACTIVATING MECHANISM FOR A MEDICAMENT DELIVERY DEVICE AND MEDICAMENT DELIVERY DEVICE

(71) Applicant: Sanofi, Paris (FR)

(72) Inventor: Michael Helmer, Frankfurt am Main (DE)

(73) Assignee: Sanofi, Paris (FR)

( * ) Notice: Subject to any disclaimer, the term of this patent is extended or adjusted under 35 U.S.C. 154(b) by 215 days.

(21) Appl. No.: 15/315,661

(22) PCT Filed: Jun. 3, 2015

(86) PCT No.: PCT/EP2015/062451
§ 371 (c)(1),
(2) Date: Dec. 1, 2016

(87) PCT Pub. No.: WO2015/185664
PCT Pub. Date: Dec. 10, 2015

(65) Prior Publication Data
US 2017/0304542 A1    Oct. 26, 2017

(30) Foreign Application Priority Data

Jun. 5, 2014   (EP) .................................... 14305855

(51) Int. Cl.
*A61M 5/24* (2006.01)
*A61M 5/32* (2006.01)

(52) U.S. Cl.
CPC ........ *A61M 5/2466* (2013.01); *A61M 5/3204* (2013.01); *A61M 5/326* (2013.01);
(Continued)

(58) Field of Classification Search
CPC .. A61M 5/2466; A61M 5/326; A61M 5/3204; A61M 2005/36; A61M 2005/2474; A61M 2005/247
See application file for complete search history.

(56) References Cited

U.S. PATENT DOCUMENTS

| 2003/0014018 | A1 | 1/2003 | Giamattista et al. |
| 2012/0041368 | A1* | 2/2012 | Karlsson ............... A61M 5/326 604/111 |
| 2014/0243741 | A1* | 8/2014 | Kaufmann .......... A61M 5/2066 604/88 |

FOREIGN PATENT DOCUMENTS

| CN | 102458537 | 5/2012 |
| CN | 103118723 | 5/2013 |

(Continued)

OTHER PUBLICATIONS

International Search Report and Written Opinion in International Application No. PCT/EP2015/062451, dated Jul. 6, 2015, 10 pages.

(Continued)

*Primary Examiner* — Bradley J Osinski
*Assistant Examiner* — Hamza A Darb
(74) *Attorney, Agent, or Firm* — Fish & Richardson P.C.

(57) ABSTRACT

The disclosure relates to an activating mechanism for a medicament delivery device, comprising an outer body, a cartridge containing a dosage of a medicament and sealed with a sealing element that is arranged across an open distal end of the cartridge, a cartridge carrier adapted to hold the cartridge, a needle safety mechanism adapted to hold a double-ended hollow needle and to relatively move along a longitudinal axis with respect to the cartridge and to the outer body to cover or to expose the needle, wherein in an initial position of the medicament delivery device, the double-ended hollow needle is spaced from the cartridge in a distal direction, and wherein when the needle safety mechanism is pressed into the outer body, a proximal end of the needle pierces the sealing element. The disclosure further relates to a medicament delivery device comprising such an activating mechanism.

16 Claims, 3 Drawing Sheets

(52) U.S. Cl.
CPC ............ *A61M 2005/247* (2013.01); *A61M 2005/2474* (2013.01); *A61M 2005/3267* (2013.01)

(56) References Cited

FOREIGN PATENT DOCUMENTS

| | | |
|---|---|---|
| EP | 0787501 | 8/1997 |
| WO | WO 99/30759 | 6/1999 |
| WO | WO 02/09797 | 2/2002 |
| WO | WO 2007/011888 | 1/2007 |
| WO | WO 2010/126432 | 11/2010 |
| WO | WO 2011/039230 | 4/2011 |
| WO | WO 2012/022810 | 2/2012 |
| WO | WO 2013/063707 | 5/2013 |

OTHER PUBLICATIONS

International Preliminary Report on Patentability in International Application No. PCT/EP2015/062451, dated Dec. 6, 2016, 7 pages.

\* cited by examiner

ACTIVATING MECHANISM FOR A MEDICAMENT DELIVERY DEVICE AND MEDICAMENT DELIVERY DEVICE

CROSS-REFERENCE TO RELATED APPLICATIONS

This application is a U.S. national stage application under 35 USC § 371 of International Application No. PCT/EP2015/062451, filed on Jun. 3, 2015, which claims priority to European Patent Application No. 14305855.0 filed on Jun. 5, 2014, the entire contents of which are incorporated herein by reference.

TECHNICAL FIELD

The disclosure relates to an activating mechanism for a medicament delivery device and a medicament delivery device incorporating such an activating mechanism.

BACKGROUND

Administering an injection is a process which presents a number of risks and challenges for users and healthcare professionals, both mental and physical. Pre-filled syringes with a syringe cartridge containing a selected dosage of a medicament for administering the medicament to a patient are known in the art. The cartridges may be stored in a blistered package so that they keep sterile until the time of use. The cartridges include a hollow injection needle that is in fluid communication with the medicament stored in the cartridge. Thus, the injection needle can be clogged after a long-term storage.

There remains a need for an improved activating mechanism for a medicament delivery device and an improved medicament delivery device incorporating such an activating mechanism.

SUMMARY

Some aspects of the disclosure can be implemented to provide an improved activating mechanism for a medicament delivery device and an improved medicament delivery device incorporating such an activating mechanism.

According to the present disclosure, there is provided an activating mechanism for a medicament delivery device comprising an outer body and a cartridge containing a dosage of a medicament and sealed with a sealing element that is arranged across an open distal end of the cartridge.

The activating mechanism further comprises a cartridge carrier that is adapted to hold the cartridge and a needle safety mechanism that is adapted to hold a double ended hollow needle and to relatively move along a longitudinal axis with respect to the cartridge and to the outer body to cover or to expose the needle. Thereby, in an initial position of the medicament delivery device, the double ended hollow needle is spaced from the cartridge in a distal direction, wherein when the needle safety mechanism is pressed into the outer body; a proximal end of the needle pierces the sealing element of the cartridge.

The provided activating mechanism for the medicament delivery device enables a reliable delivery of the medicament into a patient. The double-ended hollow needle gets in contact with the medicament immediately before the start of the injection process. Thus, a risk for a clogged needle by the medicament is minimized compared with the related art, whereby an injection time will not be increased. In the related art, the needle can be clogged by the medicament stored in the cartridge due to a long-time storage, when the needle is in contact with the medicament all the time. With the provided preassembling of the double-ended hollow needle and the needle safety mechanism, the double-ended hollow needle will keep sterile and clean until the beginning of an injection process. The needle safety mechanism may comprise one or more sleeves that are movable with respect to the outer body and the cartridge, thus the sealing element of the cartridge is pierced by the double-ended hollow needle. Here, the initial position of the medicament delivery device is a position in which the medicament delivery device would be presented to the user prior to use, whereby the double-ended hollow needle is not in fluid communication with the medicament stored in the cartridge. The sealing element seals the medicament stored in the cartridge against environmental influences and ensures that the medicament remains within the cartridge.

In an exemplary embodiment, the needle safety mechanism comprises an outer needle sleeve and an inner needle sleeve. The outer needle is adapted to centre the inner needle sleeve and the cartridge carrier within the outer needle sleeve. In addition, the outer needle sleeve is adapted to cover or to expose the double-ended hollow needle. The inner needle sleeve is adapted to hold the double-ended hollow needle.

During activation of the medicament delivery device, the inner needle sleeve and the outer needle sleeve are commonly moved with respect to the cartridge, thus allowing the double-ended hollow needle to pierce the sealing element of the cartridge.

Therefore, the double ended hollow needle comprises the proximal end and a distal end, whereby the proximal end pierces the sealing element of the cartridge during activation of the medicament delivery device and the distal end pierces an injection site, e. g. a patient's skin.

In an exemplary embodiment, the inner needle sleeve comprises at least one rib protruding radially inwards, wherein the at least one rib is engaged in a first recess that is arranged on an outer surface of the cartridge carrier. The at least one rib as well as the first recess may be formed circular, thus the rib is designed as a circular collar. In an alternative embodiment, the inner needle sleeve comprises a number of ribs that engage in a corresponding number of first recesses. Thus, the cartridge holder and the cartridge are reliably held within the inner needle sleeve.

In an exemplary embodiment, the rib and the first recess have various dimensions and are correspondingly adapted in such a manner that the inner needle sleeve is movable with respect to the cartridge carrier a predetermined distance, wherein the distance is determined by a length expansion of the first recess. In particular, the length expansion of the rib is smaller than the length expansion of the first recess, whereby the length expansions extend along the longitudinal axis. Thereby, the inner needle sleeve is proximally movable with respect to the cartridge carrier until the rib abuts against a proximal end of the first recess. This implies a relative movement of the needle relating to the cartridge carrier including the cartridge. Due to this, the needle pierces the sealing element of the cartridge, thus the needle gets in fluid communication with the medicament stored in the cartridge.

The outer needle sleeve comprises at least one resilient arm comprising a first section that protrudes radially inwards and that is provided to engage with a second recess arranged on an outer surface of the inner needle sleeve. The resilient arm further comprises a second section that protrudes radially outwards and that bears against an inner surface of the outer body. The engagement of the resilient arm and the second recess enables a common movement of the outer needle sleeve and the inner needle sleeve during activating the medicament delivery device, wherein the needle is still covered by the outer needle sleeve. A release of this engagement, by which the outer needle sleeve is free to move along the longitudinal axis, in particular in the proximal direction, with respect to the inner needle sleeve, causes an exposing of the needle. The outer needle sleeve may comprise one or more resilient arms that are arranged around the circumference. Alternatively, the resilient arm may be designed as a circular spring collar, whereby the second recess is correspondingly designed as a circular recess.

For releasing the engagement between the inner needle sleeve and the outer needle sleeve, the at least one resilient arm is arranged to move outwards in a third recess arranged on an inner surface of the outer body. The at least one resilient arm moves into the third recess by moving the outer needle sleeve with respect to the outer body in the proximal direction until the resilient arms are at the same level as the third recess, regarding to the longitudinal axis. The at least one resilient arm is axially guidable within the third recess in the proximal direction until the second section of the at least one resilient arm abuts against a proximal end of the third recess. With this, the needle can be exposed by a further proximal movement of the outer needle sleeve with respect to the inner needle sleeve and the outer body.

In an exemplary embodiment, the outer needle sleeve comprises a removable sealing foil that is arranged across an open distal end. The sealing foil seals the injection needle against environmental influences, thus the injection needle keeps sterile until the injection process starts. For starting the injection process, the sealing foil has to be removed. The removal of the sealing foil can be easily performed manually. In an exemplary embodiment, the sealing foil comprises a removing aid.

The activating mechanism further comprises a piston rod that is adapted to engage with a stopper for displacing the stopper within the cartridge. By displacing the stopper within the cartridge in the distal direction, the medicament stored in the cartridge is ejected through the injection needle into an injection side of the patient. The piston rod may be connected to a button for automatic medicament delivery. In another exemplary embodiment, the piston rod may be guided by a manual force.

A medicament delivery device comprising an activating mechanism as it is described before, is suitable for use as a pen-type device with an automatic needle insertion and/or an automatic medicament delivery.

Further scope of applicability of the present disclosure will become apparent from the detailed description given hereinafter. However, it should be understood that the detailed description and specific examples, while indicating exemplary embodiments, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given hereinbelow and the accompanying drawings which are given by way of illustration only, and thus, are not limitive of the present disclosure, and wherein.

Corresponding parts are marked with the same reference symbols in all figures.

DETAILED DESCRIPTION

In the present application, when the term "distal section/end" is used, this refers to the section/end of the medicament delivery device, or the sections/ends of the components thereof, which under use of the medicament delivery device is located the furthest away from the medicament delivery site of the patient. Correspondingly, when the term "proximal section/end" is used, this refers to the section/end of the medicament delivery device, or the sections/ends of the components thereof, which under use of the medicament delivery device is located closest to the medicament delivery site of the patient.

Figure 1:
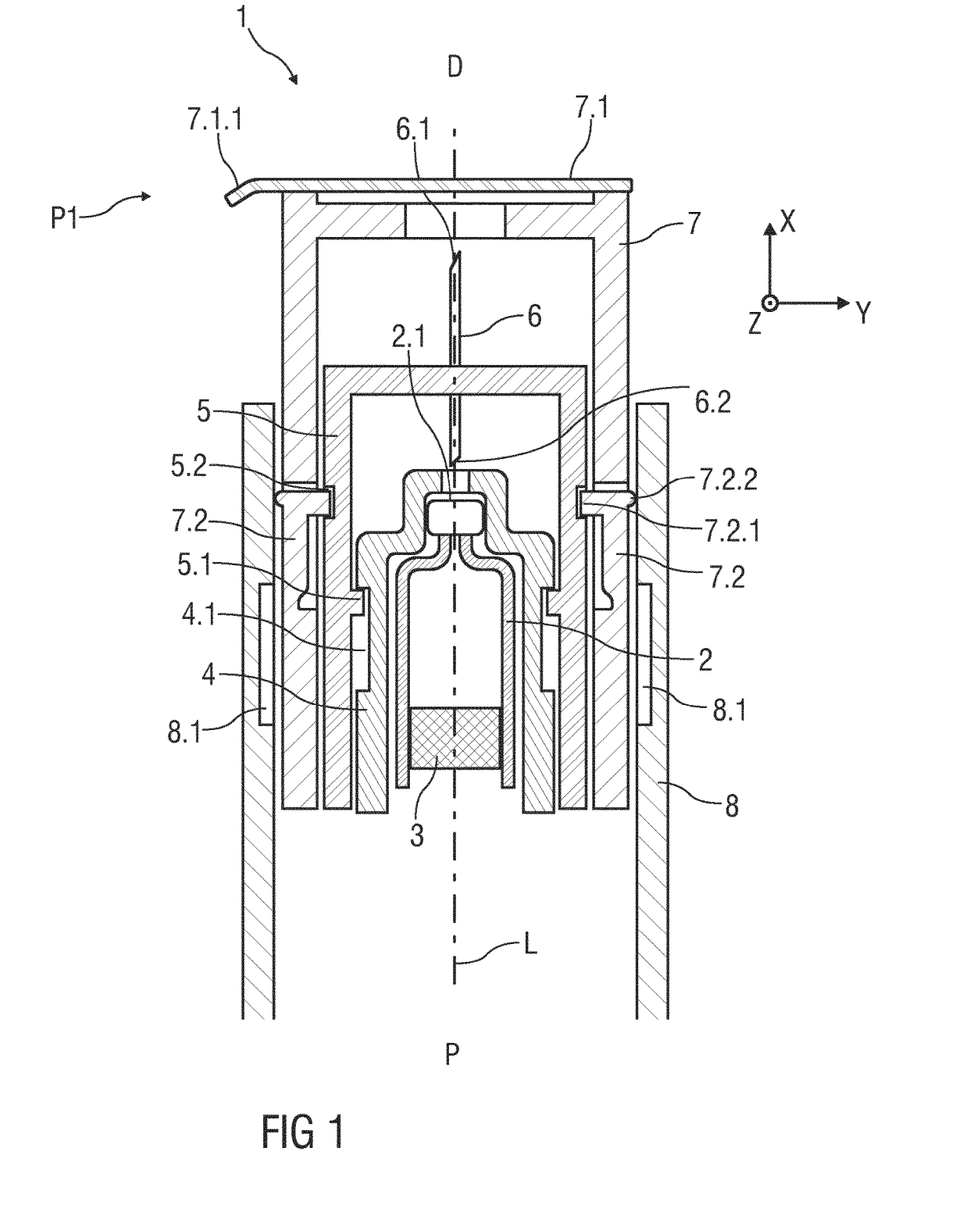
FIG. 1 is a schematic longitudinal section view of an exemplary embodiment of a medicament delivery device in an initial position.
Figure 2:
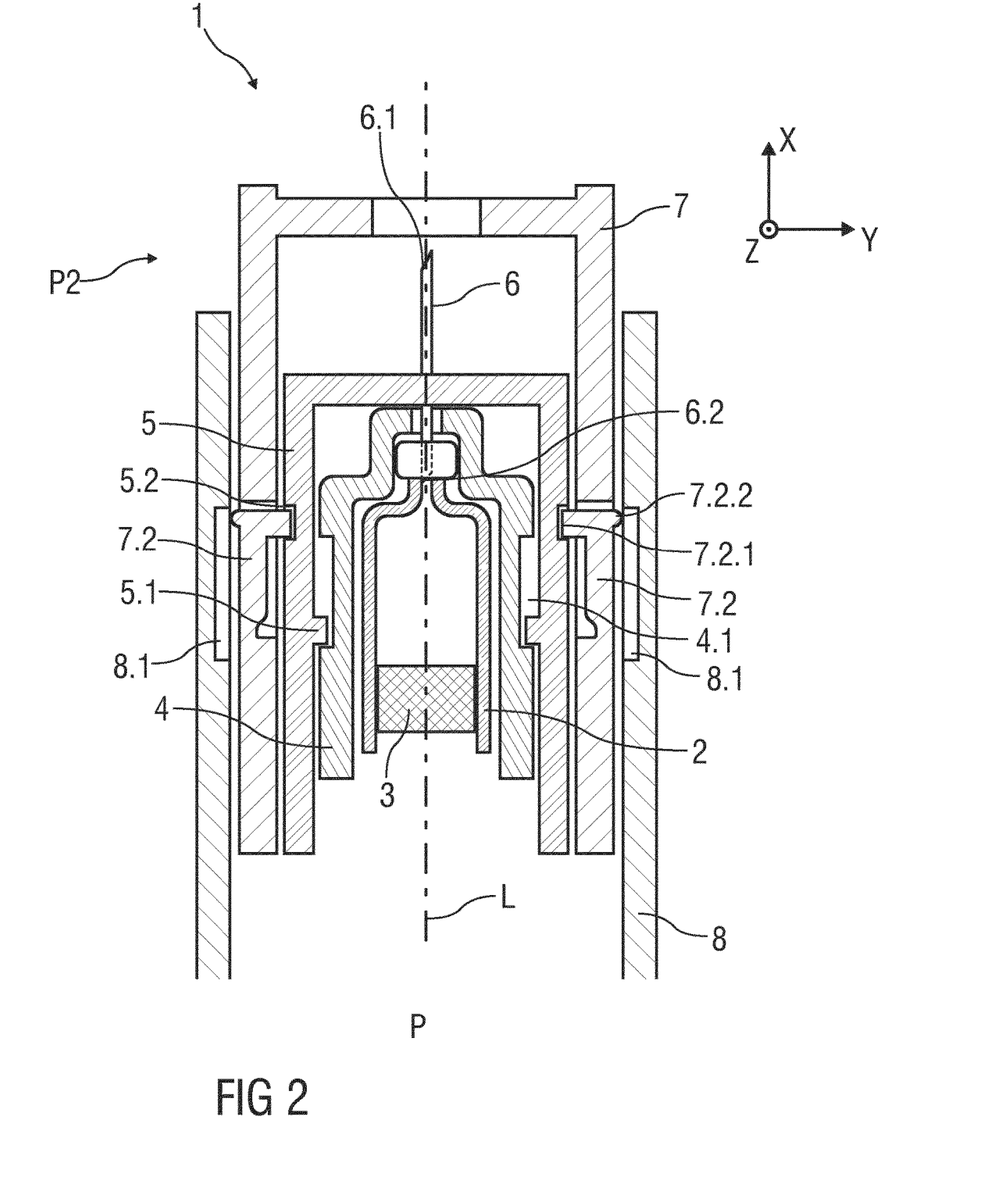
FIG. 2 is a schematic longitudinal section view of an exemplary embodiment of a medicament delivery device in a first operating position.

By way of illustration, a cartesian coordinate system with the coordinates x, y and z is illustrated in all FIGS. 1 and 2.

FIG. 1 shows a schematic longitudinal section view of an exemplary embodiment of a medicament delivery device 1, whereby the medicament delivery device 1 is in an initial position P1.

In context of the present application, the initial position P1 of the medicament delivery device 1 is a position in which the medicament delivery device 1 would be presented to the user prior to use before starting an injection process.

The medicament delivery device 1 comprises a cartridge 2 forming a cavity that contains a selected dosage of a medicament. The cartridge 2 comprises a cylindrically shaped main outer body and a neck section on a distal end of the main outer body. The distal end of the cartridge 2 comprises a flange to retain a sealing element 2.1, e. g. a fluid impermeable membrane or foil, that is arranged across the open distal end of the cartridge 2. The sealing element 2.1 seals the medicament distally against environmental influences and ensures that the medicament remains within the cartridge 2. The medicament is further proximally sealed by a stopper 3 that is disposed within the cartridge 2 on a proximal end when the medicament delivery device 1 is in the initial position P1.

The cartridge 2 is held in a substantially cylindrical shaped cartridge carrier 4 that comprises a hollow main outer body for receiving the main outer body of the cartridge 2 and an open tapering distal end for receiving the flange of the cartridge 2, whereby an inner diameter of the tapering distal end is smaller than a maximum outer diameter of the cartridge 2. Thus, a shoulder of the cartridge 2 abuts against a bottom end of the main outer body of the cartridge holder 4. In a not shown exemplary embodiment, the cartridge holder 4 comprises proximally a ridge that protrudes radially inwards and that is adapted to engage the cartridge 2 for restricting movement along a longitudinal axis L of the medicament delivery device 1 in a proximal direction P relative to the cartridge carrier 4.

The cartridge holder 4 is further provided with a first recess 4.1 that is arranged around the circumference of an outer surface of the cartridge holder 4 main outer body and that reduces the outer diameter of the cartridge carrier 4. In an alternative embodiment, the first recess 4.1 may be arranged section-wise around the circumference of the cartridge holder 4 main outer body. The first recess 4.1 is arranged to engage the cartridge holder 4 with an inner needle sleeve 5. The inner needle sleeve 5 is designed as a hollow sleeve that encloses the cartridge carrier 4.

To realize an engagement of the cartridge carrier 4 and the inner needle sleeve 5, the inner needle sleeve 5 comprises a circular rib 5.1 that protrudes radially inwards. The rib 5.1 engages in the first recess 4.1, whereby a length expansion of the rib 5.1 is smaller than a length expansion of the first recess 4.1. Thus, the inner needle sleeve 5 is allowed to move axially with respect to the cartridge carrier 4, whereby the first recess 4.1 serves as a linear guide and as an anti-rotation lock. In context of the present application, the mentioned length expansions extend along the longitudinal axis L of the medicament delivery device 1.

While the medicament delivery device 1 is in the initial position P1, the rib 5.1 is arranged on a proximal end of the first recess 4.1. At the beginning of an injection process, the inner needle sleeve 5 is allowed to move in a proximal direction P with respect to the cartridge carrier 4 as it is described in more detail in the description of FIG. 2.

Furthermore, the inner needle sleeve 5 comprises a hollow injection needle 6 that is arranged throughout a distal end of the inner needle sleeve 5. The injection needle 6 thus is divided into an outer needle section 6.2 and an inner needle section 6.1.

The outer needle section 6.2 comprises a needle tip that is targeted outside the inner needle sleeve 5 in the distal direction D. The inner needle section 6.1 comprises a needle tip that is targeted inside the inner needle sleeve 5 in the proximal direction P. The needle tip of the inner needle section 6.1 is distally spaced from the cartridge 2 and the cartridge carrier 4 when the medicament delivery device 1 is in the initial position. In particular, the injection needle 6 is not in fluid communication with the medicament before the injection begins.

The outer needle tip 6.2 is sealed against environmental influences by a removable sealing foil 7.1 that is arranged across a distal end of an outer needle sleeve 7 which encloses the inner needle sleeve 5. The sealing foil 7.1 is designed as a fluid impermeable membrane equivalent to the sealing element 2.1 of the cartridge 2. The sealing foil 7.1 can be easily removed at the beginning of the injection process by pulling off the sealing foil 7.1 with the help of a removal aid 7.1.1. The distal end of the outer needle sleeve 7 comprises an opening that is aligned to the injection needle 6.

The outer needle sleeve 7 further comprises two resilient arms 7.2 that are formed as tongues, cut out in a window-like way respectively and that are circumferentially spaced apart from each other. The free ends of the resilient arms 7.2 are hooked-shape and comprise a first section 7.2.1 that protrudes radially inside, respectively. The first sections 7.2.1 engage in a corresponding number of second recesses 5.2 that are arranged on an outer surface of the inner needle sleeve 5. Respectively, the free ends of the resilient arms 7.2 further comprise a second section 7.2.2 that is arranged opposite to the first section 7.2.1 and that protrudes radially outwards, bearing against an inner surface of a substantially elongated and cylindrical outer body 8 of the medicament delivery device 1, which encloses the outer needle sleeve 7 section-wise, whereby the outer needle sleeve 7 is guided by the outer body 8. In the initial position P1, the outer needle sleeve 7 projects beyond the outer body 8 in the proximal direction P.

In an alternative embodiment, the resilient arms 7.2 may be formed as a circular spring collar that engages in a circular formed second recess 5.2.

The resilient arms 7.2 and the second recesses 5.2 form a releasable engagement between the outer needle sleeve 7 and the inner needle sleeve 5.

For the release of this engagement, the outer body 8 comprises a number of third recesses 8.1 corresponding with a number of resilient arms 7.2. The third recesses 8.1 are arranged on the inner surface of the outer body 8 and respectively have a length extension that corresponds substantially with the projection length of the outer needle sleeve 7 with respect to the outer body 8 in the initial position P1.

By moving the outer needle sleeve 7 in the proximal direction P with respect to the outer body 8, the resilient arms 7.2 jump outside the second recesses 5.2 into the third recesses 8.1 until they are at the same level as a distal end of the third recesses 8.1, regarding to the longitudinal axis L. The outward jumping of the resilient arms 7.2 is due to the force generated by the outer needle sleeve 7. The released engagement enables an exposing of the injection needle 6 as it is described in more detail in the description of FIG. 3.

FIG. 2 shows a schematic longitudinal section view of an exemplary embodiment of the medicament delivery device 1, whereby the medicament delivery device 1 is in a first operating position P2 for starting the injection process.

In order to perform the injection process, the medicament delivery device 1 may be operated according to the following exemplary method.

The sealing foil 7.1 is removed from the distal end of the outer needle sleeve 7 by pulling off the sealing foil 7.1 by means of the removal aid 7.1.1.

The injection needle 6 is located within the outer needle sleeve 7, preventing a user from touching and seeing it. In this state, the medicament delivery device 1 may be held at the outer body 8 and the outer needle sleeve 7 is pushed against an injection site, e.g. a patient's skin. Consequently, the outer needle sleeve 7 and the inner needle sleeve 5 commonly move into the proximal direction P relative to the outer body 8 and to the cartridge carrier 4 against a force of a not shown spring by which the outer needle sleeve 7 is supported.

Referring to the exemplary embodiment that is shown in FIG. 2, the distance the outer needle sleeve 7 and the inner needle sleeve 5 has been moved in the proximal direction P corresponding with a length of the first recess 4.1 of the cartridge carrier 4. The rib 5.1 of the inner needle sleeve 5 abuts against the proximal end of the first recess 4.1, thus the cartridge carrier 4 can be moved together with the inner needle sleeve 5 in the proximal direction P, when the outer needle sleeve 7 is moved further in the proximal direction P.

Because the length of the first recess 4.1 is smaller than a length by which the outer needle sleeve 7 projects beyond the outer body 8, the outer needle section 6.2 is still covered by the outer needle sleeve 7. The needle tip of the inner needle section 6.1 is in fluid communication with the medicament, since, due to the proximal movement of the inner needle sleeve 5 including the injection needle 6, the needle tip of the inner needle section 6.1 has pierced the sealing element 2.1 of the cartridge 2 after passing the open end of the cartridge carrier 4.

The resilient arms 7.2 of the outer needle sleeve 7 has reached the area of the third recesses 8.1 of the outer body 8, thus the resilient arms 7.2 jump out of the second recesses 5.2. This is possible, as the hooked free ends of the resilient arms 7.2 are at the same level as the third recesses 8.1, regarding to the longitudinal axis L.

The inner needle sleeve 5 and the outer needle sleeve 7 are released from each other. A further proximal movement of the outer needle sleeve 7 for exposing the injection needle 6 is described below in the description of FIG. 3.

Figure 3:
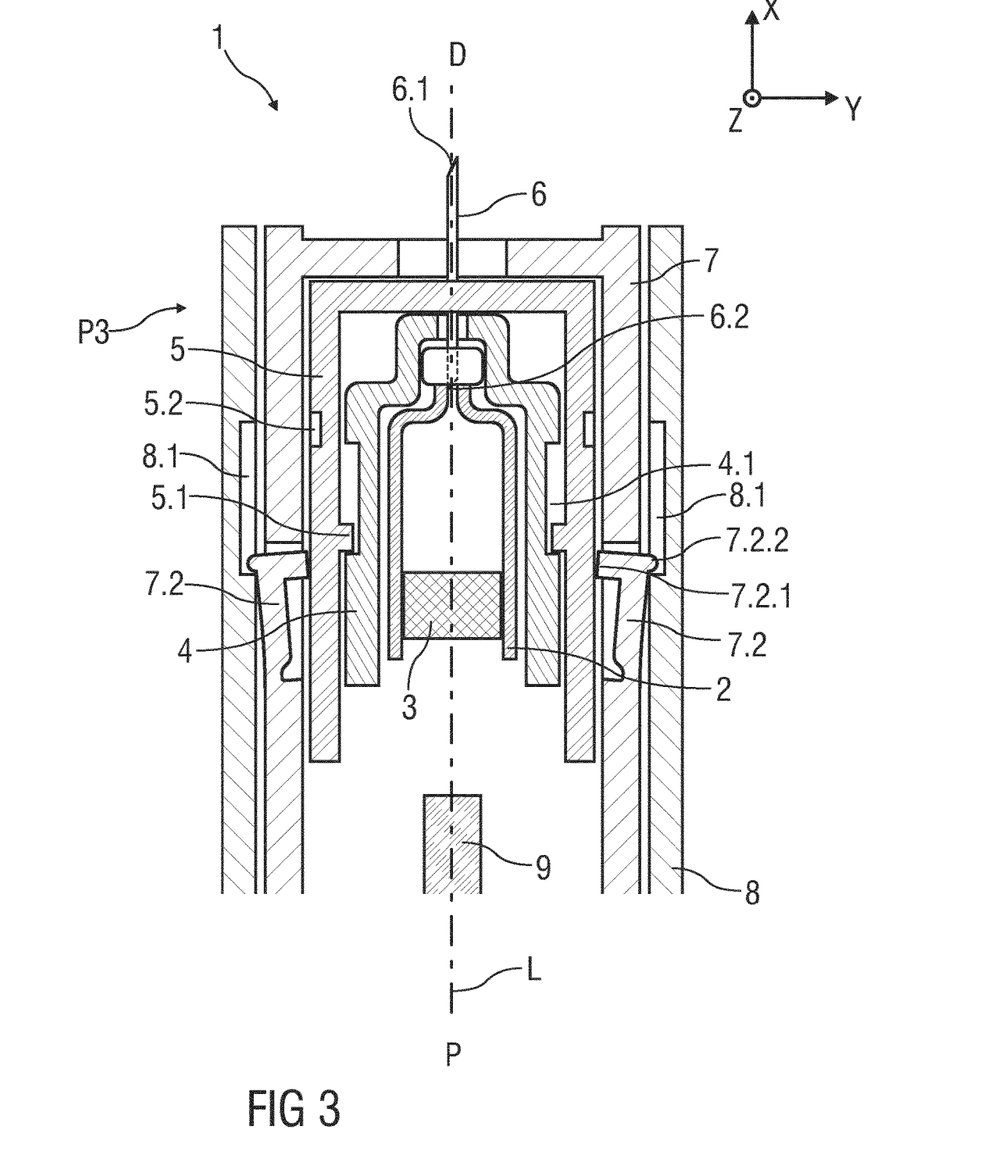
FIG. 3 is a schematic longitudinal section view of an exemplary embodiment of a medicament delivery device according to the present invention in a second operating position.

FIG. 3 shows a schematic longitudinal section view of an exemplary embodiment of the medicament delivery device 1, whereby the medicament delivery device 1 is in a second operating position P3 ready for ejection of the medicament into the injection site.

By a further proximal movement of the outer needle sleeve 7 starting from the first operating position P2 as shown in FIG. 2, the inner needle sleeve 5 including the injection needle 6 and the cartridge carrier 4 stay in position relative to the outer body 8 while the outer needle sleeve 7 moves further in the proximal direction P. Hence, the injection needle 6 is exposed and may be inserted into the injection site, whereby an insertion depth of the injection needle 6 is provided by a force applied by a user of the medicament delivery device 1.

Because the outer needle sleeve 7 is free to move in the proximal direction P with respect to the outer body 8, the inner needle sleeve 5 and the cartridge carrier 4 until the second section 7.2.2 of the resilient arms 7.2 abut against a proximal end of the third recesses 8.1.

The ejection of the medicament starts by engaging a piston rod 9 with the stopper 3, whereby the piston rod 9 displaces the stopper 3 within the cartridge 2 in the distal direction D. The piston rod 9 may be driven by a power unit of a not shown autoinjector device or by a manual force.

After that, the medicament delivery device 1 may be removed from the injection site, whereby a needle covering mechanism may be activated for covering the injection needle 6 after the injection process, for example by a distal movement of the outer needle sleeve 7.

In the illustrated embodiments the medicament delivery device 1 may be provided with manual needle insertion and manual medicament delivery. Likewise, the medicament delivery device 1 could be provided with automatic needle insertion and/or automatic medicament delivery in order to adjust the injection force.

The term "drug" or "medicament", as used herein, means a pharmaceutical formulation containing at least one pharmaceutically active compound,
wherein in one embodiment the pharmaceutically active compound has a molecular weight up to 1500 Da and/or is a peptide, a proteine, a polysaccharide, a vaccine, a DNA, a RNA, an enzyme, an antiouter body or a fragment thereof, a hormone or an oligonucleotide, or a mixture of the above-mentioned pharmaceutically active compound,
wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis,
wherein in a further embodiment the pharmaceutically active compound comprises at least one peptide for the treatment and/or prophylaxis of diabetes mellitus or complications associated with diabetes mellitus such as diabetic retinopathy,
wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antiouter body is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antiouter body; these chains are found in IgA, IgD, IgE, IgG, and IgM antibodies, respectively.

Distinct heavy chains differ in size and composition; α and γ contain approximately 450 amino acids and δ approximately 500 amino acids, while p and E have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and a have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antiouter body contains two light chains that are always identical; only one type of light chain, κ or λ, is present per antiouter body in mammals.

Although the general structure of all antibodies is very similar, the unique property of a given antiouter body is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antiouter body fragment" contains at least one antigen binding fragment as defined above, and exhibits essentially the same function and specificity as the complete antiouter body of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present disclosure, which encompass such modifications and any and all equivalents thereof.

LIST OF REFERENCES 1 medicament delivery device
2 cartridge
2.1 sealing element
3 stopper
4 cartridge holder
4.1 first recess
5 inner needle sleeve
5.1 rib
6 needle
6.1 inner needle section
6.2 outer needle section
7 outer needle sleeve
7.1 sealing foil
7.2 resilient arm
7.2.1 first section
7.2.2 second section
8 outer body
8.1 third recess
9 piston rod
D distal direction
L longitudinal axis
P proximal direction
x, y, z cartesian coordinates

The invention claimed is:

1. An activating mechanism for a medicament delivery device, comprising:
an outer body,
a cartridge containing a dosage of a medicament and sealed with a sealing element that is arranged across an open distal end of the cartridge,
a cartridge carrier adapted to hold the cartridge,
a needle safety mechanism adapted to hold a double-ended hollow needle and to relatively move along a longitudinal axis with respect to the cartridge and to the outer body to cover or to expose the double-ended hollow needle,
wherein in an initial position of the medicament delivery device, the double-ended hollow needle is spaced from the cartridge in a distal direction, and
wherein when the needle safety mechanism is pressed into the outer body, a proximal end of the double-ended hollow needle pierces the sealing element,
wherein the needle safety mechanism comprises an inner needle sleeve and an outer needle sleeve, and
wherein the outer needle sleeve comprises at least one resilient arm that comprises:
a first section that protrudes radially inwards and that is provided to engage with a second recess arranged on an outer surface of the inner needle sleeve, and
a second section that protrudes radially outwards and that bears against an inner surface of the outer body.

2. The activating mechanism according to claim 1, wherein during activation of the medicament delivery device, the inner needle sleeve and the outer needle sleeve are commonly movable with respect to the cartridge.

3. The activating mechanism according to claim 1, wherein the double-ended hollow needle comprises the proximal end and a distal end.

4. The activating mechanism according to claim 1, wherein the inner needle sleeve comprises at least one rib protruding radially inwards, and wherein the at least one rib engages in a first recess that is arranged on an outer surface of the cartridge carrier.

5. The activating mechanism according to claim 4, wherein the at least one rib and the first recess are correspondingly adapted in such a manner that the inner needle sleeve is axially movable with respect to the cartridge carrier a predetermined distance, whereby the predetermined distance is determined by a length expansion of the first recess.

6. The activating mechanism according to claim 5, wherein the inner needle sleeve is proximally movable with respect to the cartridge carrier until the at least one rib abuts against a proximal end of the first recess.

7. The activating mechanism according to claim 1, wherein the at least one resilient arm is adapted to move outwards into a third recess that is arranged on an inner surface of the outer body.

8. The activating mechanism according to claim 7, wherein the at least one resilient arm is axially guidable within the third recess.

9. The activating mechanism according to claim 7, wherein the outer needle sleeve is proximally movable with respect to the outer body until the second section of the at least one resilient arm abuts against a proximal end of the third recess.

10. The activating mechanism according to claim 7, wherein the engagement of the outer needle sleeve and the inner needle sleeve is releasable when the at least one resilient arm moves outwards into the third recess.

11. The activating mechanism according to claim 1, wherein an outer needle sleeve comprises a removable sealing foil that is arranged across an open distal end of the outer needle sleeve.

12. The activating mechanism according to claim 1, further comprising a piston rod that is adapted to engage with a stopper for displacing the stopper within the cartridge.

13. The activating mechanism according to claim 1, wherein the medicament comprises a pharmaceutically active compound.

14. A medicament delivery device comprising an activating mechanism, the activating mechanism comprising:
an outer body,
a cartridge containing a dosage of a medicament and sealed with a sealing element that is arranged across an open distal end of the cartridge,
a cartridge carrier adapted to hold the cartridge,
a needle safety mechanism adapted to hold a double-ended hollow needle and to relatively move along a longitudinal axis with respect to the cartridge and to the outer body to cover or to expose the double-ended hollow needle,
wherein in an initial position of the medicament delivery device, the double-ended hollow needle is spaced from the cartridge in a distal direction, and
wherein when the needle safety mechanism is pressed into the outer body, a proximal end of the needle pierces the sealing element,
wherein the needle safety mechanism comprises an inner needle sleeve and an outer needle sleeve, and
wherein the inner needle sleeve comprises at least one rib protruding radially inwards, and wherein the at least one rib engages in a first recess that is arranged on an outer surface of the cartridge carrier.

15. The medicament delivery device of claim 14, wherein during activation of the medicament delivery device, the inner needle sleeve and the outer needle sleeve are commonly movable with respect to the cartridge.

16. The medicament delivery device of claim 14, wherein the at least one rib and the first recess have various dimensions and are correspondingly adapted in such a manner that the inner needle sleeve is axially movable with respect to the cartridge carrier a predetermined distance, whereby the predetermined distance is determined by a length expansion of the first recess.

* * * * *